United States Patent
Rademacher et al.

(10) Patent No.: US 8,895,023 B2
(45) Date of Patent: *Nov. 25, 2014

(54) NANOPARTICLES FOR PROVIDING IMMUNE RESPONSES AGAINST INFECTIOUS AGENTS

(71) Applicant: Midatech Limited, Oxford, Oxfordshire (GB)

(72) Inventors: Thomas William Rademacher, Oxford (GB); Phillip Williams, Oxford (GB)

(73) Assignee: Midatech Limited, Oxford (GB)

(*) Notice: Subject to any disclaimer, the term of this patent is extended or adjusted under 35 U.S.C. 154(b) by 0 days.

This patent is subject to a terminal disclaimer.

(21) Appl. No.: 13/867,238

(22) Filed: Apr. 22, 2013

(65) Prior Publication Data
US 2013/0337005 A1    Dec. 19, 2013

Related U.S. Application Data

(63) Continuation of application No. 12/296,973, filed as application No. PCT/GB2007/001377 on Apr. 13, 2007, now Pat. No. 8,425,915.

(60) Provisional application No. 60/791,746, filed on Apr. 13, 2006.

(51) Int. Cl.
*A61K 47/48* (2006.01)
*B82Y 5/00* (2011.01)
*A61K 39/385* (2006.01)
*A61K 33/24* (2006.01)
*A61K 39/00* (2006.01)

(52) U.S. Cl.
CPC . *A61K 47/48092* (2013.01); *A61K 2039/55555* (2013.01); *A61K 47/48861* (2013.01); *B82Y 5/00* (2013.01); *A61K 39/385* (2013.01); *A61K 47/48261* (2013.01); *A61K 47/4833* (2013.01); *A61K 47/48884* (2013.01); *A61K 2039/6031* (2013.01); *A61K 33/24* (2013.01)
USPC ............... 424/196.11; 424/197.11; 424/193.1

(58) Field of Classification Search
CPC ................ A61K 33/24; A61K 39/385; A61K 47/48092; A61K 47/48261; A61K 47/48861; A61K 47/48884; A61K 2039/55555; A61K 2039/6031; B82Y 5/00
See application file for complete search history.

(56) References Cited

U.S. PATENT DOCUMENTS

| | | | |
|---|---|---|---|
| 2004/0022840 | A1 | 2/2004 | Nagy et al. |
| 2005/0208470 | A1 | 9/2005 | Latz et al. |
| 2006/0233712 | A1 | 10/2006 | Penades et al. |
| 2009/0104268 | A1 | 4/2009 | Himmler et al. |

FOREIGN PATENT DOCUMENTS

| | | |
|---|---|---|
| WO | 2004108165 | 12/2004 |
| WO | 2005116226 | 12/2005 |
| WO | 2006037979 | 4/2006 |

OTHER PUBLICATIONS

W. Chen et al., "Human 60-kDa Heat-Shock Protein: A Danger Signal to the Innate Immune System", The Journal of Immunology, 1999(162): 3212-3219 (1998).
International Search Report and Written Opinion from corresponding International Application No. PCT/GB2007/001377.

*Primary Examiner* — Doug Schultz
(74) *Attorney, Agent, or Firm* — Patrick J. Hagan; Dann, Dorfman, Herrell and Skillman

(57) ABSTRACT

Nanoparticles for providing immune responses for the treatment or prophylaxis of infection by infectious agents such as viruses, parasites, bacteria, prions and fungi are described which comprises a core including metal and/or semiconductor atoms, wherein the core is covalently linked to a plurality of ligands, the ligands including a carbohydrate residue capable of stimulating an innate immune response, a T cell helper peptide and a danger signal. This platform may then be adapted by including one or more further ligands capable of producing a specific response to a target infectious agent.

5 Claims, 3 Drawing Sheets

SEQUENCE LISTING

<160> NUMBER OF SEQ ID NOS: 65

<210> SEQ ID NO 1
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 1

Phe Lys Leu Gln Thr Met Val Lys Leu Phe Asn Arg Ile Lys Asn Asn
 1               5                  10                  15

Val Ala

```
<210> SEQ ID NO 2
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 2

Gly Val Ser Ser Ala
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 3

Asn Gly Gln Ser Gly Arg
1               5

<210> SEQ ID NO 4
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 4

Tyr Ile Val Glu Lys Ala Asn Pro Val Asn Asp Leu
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 5

Tyr Pro Gly Asp Phe Asn Asp Tyr Glu Glu Leu
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 6

Glu Lys Ile Gln Ile Ile Pro Lys Ser Ser
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 7

Pro Tyr Gln Gly Lys Ser Ser Phe Phe Arg Asn Val
1               5                   10
```

```
<210> SEQ ID NO 8
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 8

Pro Asn Asp Ala Ala Glu Gln Thr Lys Leu Tyr Gln
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 9

Ser Thr Leu Asn Gln Arg Leu Val Pro Arg
1               5                   10

<210> SEQ ID NO 10
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 10

Leu Lys Pro Asn Asp Ala Ile Asn Phe Glu Ser Asn Gly Asn Phe Ile
1               5                   10                  15

Ala

<210> SEQ ID NO 11
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 11

Glu Ser Asn Gly Asn Phe Ile Ala Pro Glu Tyr Ala
1               5                   10

<210> SEQ ID NO 12
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 12

Ala Pro Glu Tyr Ala Tyr Lys Ile Val Lys Lys Gly Asp Ser Thr Ile
1               5                   10                  15

<210> SEQ ID NO 13
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 13

Ser Asn Glu Gln Gly Ser Gly Tyr Ala Ala Ala
1               5                   10
```

```
<210> SEQ ID NO 14
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 14

Ala Val Gly Arg Glu Phe Asn Asn Leu Glu Arg
 1               5                  10

<210> SEQ ID NO 15
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 15

Asp Ser Asn Val Lys Asn Leu Tyr Asp Lys Val Arg Leu Gln
 1               5                  10

<210> SEQ ID NO 16
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 16

Glu Ala Arg Leu Lys Arg Glu Glu Ile Ser Gly Val Lys Leu Glu Ser
 1               5                  10                  15

Ile

<210> SEQ ID NO 17
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 17

Tyr Pro Gly Asp Phe Asn Asp Tyr Glu Glu
 1               5                  10

<210> SEQ ID NO 18
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 18

Asp Ala Ala Glu Gln Thr Lys Leu Tyr Gln
 1               5                  10

<210> SEQ ID NO 19
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 19

Arg Ile Ala Thr Arg Ser Lys Val Asn Gly
 1               5                  10
```

```
<210> SEQ ID NO 20
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 20

Asn Asp Ala Ile Asn Phe Glu Ser Asn Gly
 1               5                  10

<210> SEQ ID NO 21
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 21

Asp Leu Asp Gly Val Lys Pro Leu Ile Leu
 1               5                  10

<210> SEQ ID NO 22
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 22

Glu Lys Ile Gln Ile Ile Pro Lys Ser Ser
 1               5                  10

<210> SEQ ID NO 23
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 23

Ser Thr Leu Asn Gln Arg Leu Val Pro Arg
 1               5                  10

<210> SEQ ID NO 24
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 24

Glu Lys Gly Lys Trp Lys Ser Val Glu Leu
 1               5                  10

<210> SEQ ID NO 25
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 25

Gly Val Phe Gly Asp Asn Pro Arg Pro Asn Asp Gly
 1               5                  10
```

```
<210> SEQ ID NO 26
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 26

Val Glu Leu Ile Arg Gly Arg Pro Lys Glu
1               5                   10

<210> SEQ ID NO 27
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 27

Glu Leu Asp Ala Pro Asn Tyr His Tyr
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 28

Gln Met Val Gln Ala Met Arg Thr Ile
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 29

Leu Leu Phe Ala Ile Val Ser Leu Val
1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 30

Gly Met Val Ser Leu Met Leu Gln Ile
1               5

<210> SEQ ID NO 31
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 31

Leu Leu Ile Asp Gly Thr Ala Ser Leu
1               5
```

-continued

```
<210> SEQ ID NO 32
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 32

Ser Ile Ile Pro Ser Gly Pro Leu Lys
 1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 33

Ala Ala Ala Lys Glu Ser Thr Gln Lys
 1               5

<210> SEQ ID NO 34
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 34

Ser Ile His Thr Gly Asn Gln His Lys
 1               5

<210> SEQ ID NO 35
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 35

Ser Met Val Glu Ala Met Val Ser Arg
 1               5

<210> SEQ ID NO 36
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 36

Leu Tyr Lys Lys Leu Lys Arg Glu Ile
 1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 37

Ile Tyr Ser Thr Val Ala Ser Ser Leu
 1               5
```

```
<210> SEQ ID NO 38
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 38

Ala Tyr Gly Val Lys Gly Phe Ser Phe
1               5

<210> SEQ ID NO 39
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 39

Ser Tyr Leu Ile Arg Ala Leu Thr Leu
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 40

Asp Pro Asn Asn Met Asp Arg Ala Val
1               5

<210> SEQ ID NO 41
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 41

Ala Pro Glu Tyr Ala Tyr Lys Ile Val
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 42

Asn Pro Asn Lys Lys Ile Ile Thr Ile
1               5

<210> SEQ ID NO 43
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 43

Gly Pro Ala Thr Ala Gln Met Ala Leu
1               5
```

```
<210> SEQ ID NO 44
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 44

Lys Asn Val Thr Val Thr His Ala Gln Asp
1               5                   10

<210> SEQ ID NO 45
<211> LENGTH: 22
<212> TYPE: PRT
<213> ORGANISM: Artificial Sequence
<220> FEATURE:
<223> OTHER INFORMATION: Synthetic Sequence

<400> SEQUENCE: 45

Asn Gly Lys Leu Cys Asp Leu Asp Gly Val Lys Pro Leu Ile Leu Arg
1               5                   10                  15

Asp Cys Ser Val Ala Gly
            20

<210> SEQ ID NO 46
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 46

Glu Phe Ile Asn Val Pro Glu Trp Ser Tyr Ile Val Glu Lys
1               5                   10

<210> SEQ ID NO 47
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 47

Pro Val Asn Asp Leu Cys Tyr Pro
1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 48

Glu Glu Leu Lys His Leu Leu Ser Arg
1               5

<210> SEQ ID NO 49
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 49

Glu Lys Ile Gln Ile Ile Pro Lys
1               5
```

```
<210> SEQ ID NO 50
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 50

Ser Ser His Glu Val Ser Leu Gly Val Ser Ser Ala Cys Pro Tyr Gln
 1               5                  10                  15

Gly Lys

<210> SEQ ID NO 51
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 51

Phe Phe Arg Asn Trp Trp Leu
 1               5

<210> SEQ ID NO 52
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 52

Glu Asp Leu Leu Val Leu Trp Gly
 1               5

<210> SEQ ID NO 53
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 53

Glu Gln Thr Lys Leu Tyr Gln
 1               5

<210> SEQ ID NO 54
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 54

Thr Tyr Ile Ser Val Gly Thr
 1               5

<210> SEQ ID NO 55
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 55

Leu Asn Gln Arg Leu Val Pro Arg
 1               5
```

```
<210> SEQ ID NO 56
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 56

Ile Ala Pro Glu Tyr Ala Tyr Lys Ile Val Lys
1               5                   10

<210> SEQ ID NO 57
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 57

Cys Asn Thr Lys Cys Gln Thr
1               5

<210> SEQ ID NO 58
<211> LENGTH: 25
<212> TYPE: PRT
<213> ORGANISM: Artificial Sequence
<220> FEATURE:
<223> OTHER INFORMATION: Synthetic Sequence

<400> SEQUENCE: 58

Pro Phe His Asn Ile His Pro Leu Thr Ile Gly Glu Cys Pro Lys Tyr
1               5                   10                  15

Val Lys Ser Asn Arg Leu Val Leu Ala
            20                  25

<210> SEQ ID NO 59
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 59

Leu Phe Gly Ala Ile Ala Gly
1               5

<210> SEQ ID NO 60
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 60

Gly Phe Leu Asp Val Trp Thr
1               5

<210> SEQ ID NO 61
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 61

Asn Ala Glu Leu Leu Val Leu
1               5
```

```
<210> SEQ ID NO 62
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 62

Val Lys Asn Leu Tyr Asp Lys Val Arg Leu
 1               5                  10

<210> SEQ ID NO 63
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 63

Cys Phe Glu Phe Tyr His Lys Cys Asp
 1               5

<210> SEQ ID NO 64
<211> LENGTH: 38
<212> TYPE: PRT
<213> ORGANISM: Artificial Sequence
<220> FEATURE:
<223> OTHER INFORMATION: Synthetic Sequence

<400> SEQUENCE: 64

Ile Ser Gly Val Lys Leu Glu Ser Ile Gly Ile Tyr Gln Ile Leu Ser
 1               5                  10                  15

Ile Tyr Ser Thr Val Ala Ser Ser Leu Ala Leu Ala Ile Met Val Ala
             20                  25                  30

Gly Leu Ser Leu Trp Met
         35

<210> SEQ ID NO 65
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 65

Ser Asn Gly Ser Leu Gln Cys
 1               5
```

NANOPARTICLES FOR PROVIDING IMMUNE RESPONSES AGAINST INFECTIOUS AGENTS

CROSS-REFERENCE TO RELATED APPLICATIONS

This application is a continuation of U.S. patent application Ser. No. 12/296,973, filed Mar. 27, 2009 (now U.S. Pat. No. 8,425,915, issuing Apr. 23, 2013), which is the U.S. National Stage of International Application No. PCT/GB2007/001377, filed Apr. 13, 2007, which claims priority from U.S. Provisional Application No. 60/791,746, filed Apr. 13, 2006. The entire disclosure of each the aforesaid applications is incorporated by reference in the present application.

FIELD OF THE INVENTION

The present invention relates to nanoparticles, and more particularly to nanoparticles for providing immune responses for the treatment or prophylaxis of infection by infectious agents such as viruses, parasites, bacteria, prions and fungi.

BACKGROUND OF THE INVENTION

The use of carbohydrate and peptide antigens in vaccines is greatly hampered by their lack of immunogenicity when injected directly into a patient. Such antigens, when injected alone, are usually ignored by antigen-presenting cells (APCs), cleared rapidly and do not induce an immune response.

In most cases, it is also necessary to administer the antigen in combination with an adjuvant. The adjuvant may be a simple delivery system such as liposomes, which slow clearance of the antigen and make it more likely to reach and be taken up by APCs. However, this in itself is not very effective and usually needs to be combined with agents that stimulate the immune system, such as bacterial products which stimulate cytokine formation. Cytokines themselves may also be co-administered. Many of these products are too toxic or too experimental to be used in humans, and the most effective adjuvants are not approved for human use. Most of the adjuvants available for use in humans are of limited effectiveness. Finding effective adjuvants suitable for human use is a continuing challenge.

Carbohydrate antigens are of particularly weak immunogenicity because they can stimulate only B-cell and not T-cell responses. This is usually circumvented by conjugating the carbohydrate to a protein carrier. However, in order to raise an immune response it is also necessary to use an adjuvant.

Many bacteria and other pathogens are also distinguished by carbohydrate antigens which would be a good target for vaccines, if carbohydrates were not so poorly immunogenic. Improving the immunogenicity of carbohydrate antigens would thus have applications in a wide variety of therapeutic fields.

WO 02/32404 (Consejo Superior de Investigaciones Cientificas) discloses nanoparticles formed from metal or semiconductor atoms in which ligands comprising carbohydrates are covalently linked to the core of the nanoparticles. These nanoparticles are used for modulating carbohydrate mediated interactions and are soluble and non-toxic. WO 2004/108165 (Consejo Superior de Investigaciones Cientificas and Midatech Limited) discloses magnetic nanoparticles having cores comprising passive and magnetic metal atoms, the core being covalently linked to ligands. WO 2005/116226 (Consejo Superior de Investigaciones Cientificas and Midatech Limited) discloses nanoparticles which are conjugated to RNA ligands, in particular siRNA ligands.

There remains a continuing need in the art for ways of delivering antigens to patients to vaccinate them against infection by pathogenic organisms such as bacteria, viruses and parasites. In particular, vaccines often require multiple doses to be administered to individuals to provide adequate protection against infection and contain peptide or protein antigens that are difficult to formulate in stable compositions, especially where the vaccines need to be stored and used in difficult environments.

SUMMARY OF THE INVENTION

Broadly, the present invention relates to nanoparticles which are designed to provide immune responses for the prophylaxis or treatment of infection by agents such as viruses, bacteria, parasites, and fungi. The nanoparticles of the present invention generally provide strong immune response when administered to individuals and may ameliorate the need for multiple vaccinations. As the nanoparticles are synthetically constructed and generally include peptide antigens, they may also have the advantage of providing a vaccine composition having improved stability compared to the protein vaccines often used in the prior art.

Accordingly, in one aspect, the present invention provides a nanoparticle which comprises a core including metal and/or semiconductor atoms, wherein the core is covalently linked to a plurality of ligands, the ligands including:

(a) a first ligand comprising a carbohydrate residue capable of stimulating an innate immune response;
(b) a second ligand comprising a T cell helper peptide; and
(c) a third ligand comprising a danger signal.

The nanoparticles may incorporate one or more further ligands that are capable of producing a specific response to target infectious agent(s). By way of example, the ligand may comprise an antigen, e.g. a peptide antigen, from an infectious agent such as influenza, HIV, tuberculosis or malaria. Methods for the identification of suitable antigens from infectious agents are well known to those skilled in the art and may be used as ligands when designing and making the nanoparticles of the present invention. An example relating to the design of nanoparticles having peptide antigens from avian flu strain H5N1 is provided in the examples below. This vaccine may be useful for the treatment or prophylaxis of infection in humans, or in animals, such as avians including wild bird populations and farmed birds such as chickens, turkeys, ducks and geese.

In accordance with the present invention, the first ligand component of the nanoparticle, the carbohydrate residue capable of stimulating an innate immune response, is designed to make the nanoparticle appear to the immune system like a fragment of an infectious agent such as a bacteria, yeast, insect or a parasite. By way of example, carbohydrate ligands which comprise N-acetyl glucosamine (GlcNAc) may make the nanoparticles appear to the immune system like the surface group of group A from *Streptococcus*. Other examples include the use of ligands comprising carbohydrate ligands such as mannose, to make the nanoparticles appear like yeast, or xylose or fucose. Thus, unlike nanoparticles in which the carbohydrate containing ligands help to shield the nanoparticles from recognition by the immune system, the incorporation of these carbohydrate residues into the corona of the nanoparticles helps to stimulate the innate immune response from the carbohydrate-based recognition system normally resulting in lectinophagocytosis of the bacterial or yeast particle and subsequent stimulation of the innate immune response. See Rademacher et al, Chapter 11, Abnormalities in IgG Glycosylation and Immunological Disorders, Ed Isenberg & Rademacher, John Wiley, 1996, p 221-252.

The second ligand component of the nanoparticles is a ligand which comprises a T-cell helper peptide, such as promiscuous T-helper peptides employed in the examples disclosed herein that are derived from tetanus toxin (TT). This component of the nanoparticle will result in stimulation of the T-cell memory and help arms of the immune response as most individuals will already have been immunized in childhood, for example, to tetanus. Other peptides, for example from measles virus could also be used. An example of a preferred peptide moiety comprises the amino acid sequence FKLQTMVKLFNRIKNNVA (SEQ ID No. 1).

The third ligand component of the nanoparticles is a ligand comprising danger signal such as an endotoxin that is capable of initiating a danger response necessary for causing an neutralising and efficacious immune response. Danger signals are recognised by the body as foreign but do not generally initiate specific antibody or T cell responses, instead serving to gear the immune system up to the threat of possible infection. Examples of such "danger signals" include endotoxins, heat-shock proteins, nucleotides, reactive oxygen intermediates, extracellular-matrix breakdown products, neuromediators and cytokines such as interferons, and lipid moieties including gram-negative lipids. In the example shown in FIG. 1, an endotoxin which is a toll 4 receptor agonist is used to which the immune system initiates the danger response necessary to initiate a neutralising and efficacious immune response. Danger signals are described in Matzinger P (1994) Tolerance, Danger, and the Extended Family. Ann. Reviews of Immunology vol 12:991-1045 and the role of toll-like receptor agonists is discussed in Aderem, A and Ulevitch, R J (2000) Nature vol 406, 782-787.

In addition, the basic nanoparticles described above may be engineered to contain further ligands, and especially to comprise ligands that are capable of producing a specific response to a target infectious agent. By way of example, the ligand may comprise an antigen, e.g. a peptide antigen, from an infectious agent. Examples of peptide antigens from a variety of infectious agents including, but not limited to, influenza including influenza (e.g. avian influenza such as the H5N1 strain), tuberculosis, HIV and malaria. The nanoparticles shown in FIG. 1 illustrates a nanoparticle which includes ligands which comprise synthetic peptide sequences from the avian influenza H5N1 virus. In some embodiments, one or more species of nanoparticles may be employed which present antigenic ligands to present epitopes from a mixture of infectious organisms, for examples peptides from avian influenza, tuberculosis, malaria and HIV, tuberculosis, etc, through the use of nanoparticles including a plurality of antigenic ligands and/or a composition comprising a plurality of different species of nanoparticles, the different species including antigenic ligands directed against different infectious agents, thus having the advantage of providing a single vaccine that protects against a range of infectious agents. Preferred ligands of this type comprise small peptide sequences derived from infectious agents, for example having 30 amino acids or less, more preferably 20 amino acids of less and most preferably between 5 and 15 amino acids.

Apart from these three components described above, it may also be useful to include further ligands to shield other elements of the nanoparticle from recognition by the immune system, that is so that the immune response produced to the nanoparticles in vivo is specific to the target infectious agent. Most conveniently, this can be accomplished by including a carbohydrate ligands, e.g. the glucose ligands of the type discussed above.

The ligands described herein many be provided as separate species linked to the core of the nanoparticle or a single ligand species may have different parts or segments providing the different functions above. For example, this might be done to reduce the number of different ligand species coupled to the core of the nanoparticle. The ligands may be purified from natural source, or synthetically or recombinantly produced using techniques known in the art. Preferably, the ligands are made using synthetic chemistry.

The ligands typically comprise carbohydrate or peptide antigens. The nanoparticles can be used to deliver the antigens and have applications in a wide range of applications, in particular as vaccines in therapeutic applications. In preferred embodiments, the nanoparticles are also linked to adjuvants, for example T-helper stimulatory peptides or carbohydrates which stimulate the innate immune network.

The vaccination system disclosed herein has several advantages over prior art methods. The nanoparticle itself may improve the immune response to the antigen by preventing breakdown or clearance of the antigen and by providing the antigen in particulate form.

Where additional adjuvants are used, the invention permits a single delivery vehicle to be used to deliver both antigen and adjuvants, or multiple antigens or adjuvants.

The nanoparticles are of small size, small enough to be taken up by cells to allow the antigen to be presented on the cell surface. Where a T-helper peptide is also conjugated to the nanoparticle, the T-helper peptide may also be presented.

Preferably, the nanoparticles of the invention are water soluble. In preferred embodiments, the nanoparticles of the invention have a core with a mean diameter between 0.5 and 10 nm, more preferably between 1 and 2.5 nm. Preferably, the nanoparticles including their ligands has a mean diameter between 10 and 30 nm.

In addition to the ligands described above, the nanoparticles may comprise one or more further types of ligands. For example, the additional ligands, or groups or domains of ligands, may include one or more peptide, a protein domain, a nucleic acid molecule, a lipidic group, a carbohydrate group, any organic or anionic or cationic group. The carbohydrate group may be a polysaccharide, an oligosaccharide or a monosaccharide group. Preferred ligands include glycoconjugates, thereby forming glyconanoparticles. Where a nucleic acid molecule is present, the nucleic acid molecule may comprise single or double stranded DNA or RNA. In a particularly preferred embodiment, the nanoparticles comprise a membrane translocation signal to aid them in permeating through a cell membrane.

The particles may have more than one species of ligand immobilised thereon, e.g. 2, 3, 4, 5, 10, 20 or 100 different ligands. Alternatively or additionally, a plurality of different types of nanoparticles may be employed together. In preferred embodiments, the mean number of total ligands linked to an individual metallic core of the particle is at least one ligand, more preferably 20 ligands, more preferably 50 ligands, more preferably 60 ligands, and most preferably 100 ligands.

The nanoparticle may also comprise a label, such as a fluorescent group, a radionuclide, a magnetic label, a dye, a NMR active atom, or an atom which is capable of detection using surface plasmon resonance. Preferred magnetic labels include paramagnetic groups comprising $Mn^{+2}$, $Gd^{+3}$, $Eu^{+2}$, $Cu^{+2}$, $V^{+2}$, $Co^{+2}$, $Ni^{+2}$, $Fe^{+2}$, $Fe^{+3}$ or lanthanides$^{+3}$. Preferred NMR active atoms include $Mn^{+2}$, $Gd^{+3}$, $Eu^{+2}$, $cu^{+2}$, $V^{+2}$, $Co^{+2}$, $Ni^{+2}$, $Fe^{+2}$, $Fe^{+3}$ or $lanthanides^{+3}$.

The core of the nanoparticle may be a metallic core. Preferably, the metallic core comprises Au, Ag or Cu, for example an alloy selected from Au/Ag, Au/Cu, Au/Ag/Cu, Au/Pt, Au/Pd, Au/Ag/Cu/Pd, Au/Fe, Au/Cu, Au/Gd, Au/Fe/Cu, Au/Fe/Gd or Au/Fe/Cu/Gd.

In some embodiments, the core of the nanoparticle is magnetic. A preferred magnetic nanoparticle core may comprise passive metal atoms and magnetic metal atoms in the core in a ratio between about 5:0.1 and about 2:5. The passive metal may be, for example, gold, platinum, silver or copper, and the magnetic metal is iron or cobalt.

In another aspect, the present invention provides compositions comprising populations of one or more nanoparticles as described herein. In some embodiments, the populations of nanoparticles may have different densities of the same or different ligands attached to the core. In some cases, it may be desirable to encapsulate the nanoparticles to enable the delivery of a plurality of nanoparticles to a target site. Suitable encapsulation technologies are well known to those skilled in the art. The encapsulated population of nanoparticles may be of one, two, three or a plurality of different types. In a preferred embodiment, the composition comprises the nanoparticles and a pharmaceutically acceptable carrier.

In a further aspect, the present invention provides a method of producing a nanoparticle as described herein. Conveniently, the method comprises conjugating the ligands with the core of the nanoparticle by derivatising the ligand with a linker and including the derivatised ligand in a reaction mixture from which the core of the nanoparticle is synthesised. During self-assembly of the nanoparticles, the nanoparticle cores attach to the ligand via the linker. The linker may comprise a thiol group, an alkyl group, a glycol group or a peptide group. An exemplary linker group is represented by the general formula HO—$(CH_2)_n$—S—S—$(CH_2)_m$—OH wherein n and m are independently between 1 and 5. When the nanoparticles are synthesized, the —S—S— of the linker splits to form two thio linkers that can each covalently attach to the core of the nanoparticle via a —S— group. In preferred embodiments, the linker group comprises C2, C3, C4, C5, C6, C7, C8, C9, C10, C11, C12, C13 or C15 alkyl and/or C2, C3, C4, C5, C6, C7, C8, C9, C10, C11, C12, C13 or C15 glycol. The linker may be a mixed linker, for example hexaethylene glycol-C11 alkyl.

Different linkers may control whether the peptide is released or remains attached to the nanoparticle. For example, the ligands may be engineered to include a cleavage site, for example by including a peptide motif that can be recognised and cleaved in vivo. An example of this is the amino acids FK, a cathepsin cleavage site.

In one embodiment, nanoparticles having cores comprising gold atoms may be synthesised using the protocol first described in WO 02/32404 in which disulphide linkers are employed to derivatise the ligands and the derivatised ligands are reacted with $HAuCl_4$ (tetrachloroauric acid) in the presence of reducing agent to produce the nanoparticles. On this method, the disulphide protected ligand in methanol or water may be added to an aqueous solution of tetrachloroauric acid. A preferred reducing agent is sodium borohydride. These and other features of the method are described WO 02/32404.

In a further aspect, the present invention also provides nanoparticles as described herein for use in preventive or palliative therapy, and especially for the treatment or prophylaxis of infection. In particular, the nanoparticles may be for use as a vaccine.

In a further aspect, the present invention provide nanoparticles as described herein for treating an infection, such as a bacterial, viral or parasitic infection. Examples of such infectious diseases and conditions are provided below.

In one aspect, the present invention provides the use of the above defined nanoparticles for the preparation of a medicament for the treatment of a condition ameliorated by the administration of the nanoparticles. For example, the nanoparticles described herein or their derivatives can be formulated in pharmaceutical compositions, and administered to patients in a variety of forms, in particular to treat conditions ameliorated by the administration of an antigen.

Also provided is the use of nanoparticles of the invention in the preparation of a medicament for the treatment of infectious disease. The pathogen causing the disease may be viral, bacterial or parasitic.

Examples of specific uses that may be treated according to the present invention are described below, along with other applications of the nanoparticles, both in vitro and in vivo uses.

Embodiments of the present invention will now be described by way of example and not limitation with reference to the accompanying figures.

DETAILED DESCRIPTION

Nanoparticles

Figure 1:
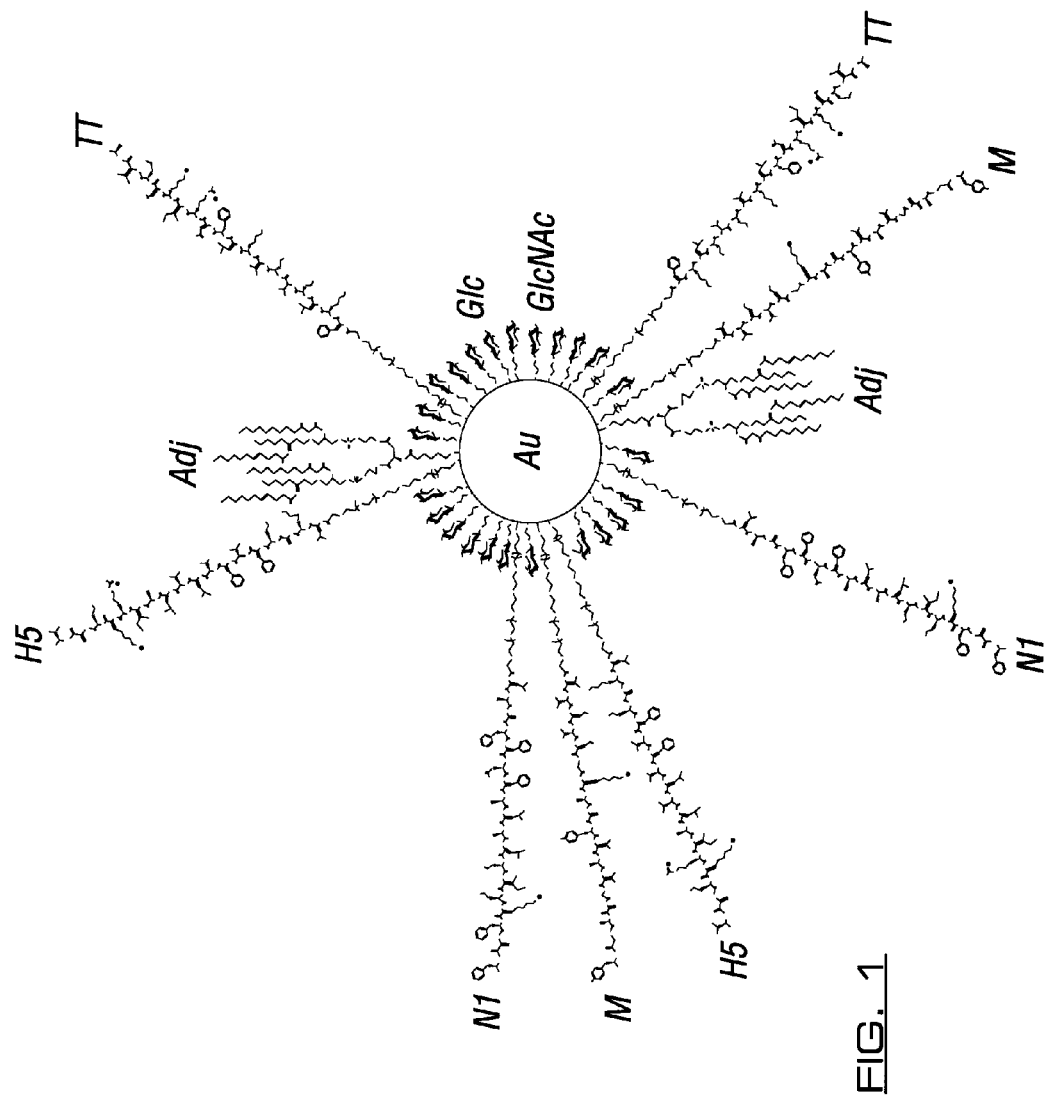
FIG. 1 shows a schematic diagram of an example of a nanoparticle for use in immunising against avian influenza. The ligands are:
Glc=glucose
GlcNAc=n-acetylglucosamine
TT=tetanus toxin (promiscuous T-helper peptide)
H5=avian influenza virus peptide antigen
N1=avian influenza virus peptide antigen
M=malaria antigen
Adj=lipid danger signal

Nanoparticles are small particles, e.g. clusters of metal or semiconductor atoms, that can be used as a substrate for immobilising ligands. They can be prepared using the methodology reported in WO 02/32404 and WO 2004/108165.

The nanoparticles of the invention are soluble in most organic solvents and especially water. This can be used in their purification and importantly means that they can be used in solution for presenting the ligand immobilised on the surface of the particle. The fact that the nanoparticles are soluble has the advantage of presenting the ligands in a natural conformation. For therapeutic applications, the nanoparticles are non toxic, soluble and stable under physiological conditions.

Preferably, the nanoparticles have cores having mean diameters between 0.5 and 50 nm, more preferably between 0.5 and 10 nm, more preferably between 0.5 and 5 nm, more preferably between 0.5 and 3 nm and still more preferably between 0.5 and 2.5 nm. When the ligands are considered in addition to the cores, preferably the overall mean diameter of the particles is between 5.0 and 100 nm, more preferably between 5 and 50 nm and most preferably between 10 and 30 nm. The mean diameter can be measured using techniques well known in the art such as transmission electron microscopy.

The core material can be a metal or semiconductor and may be formed of more than one type of atom. Preferably, the core material is a metal selected from Au, Fe or Cu. Nanoparticle cores may also be formed from alloys including Au/Fe, Au/Cu, Au/Gd, Au/Fe/Cu, Au/Fe/Gd and Au/Fe/Cu/Gd, and may be used in the present invention. Preferred core materials are Au and Fe, with the most preferred material being Au. The cores of the nanoparticles preferably comprise between about 100 and 500 atoms (e.g. gold atoms) to provide core diameters in the nanometer range. Other particularly useful core materials are doped with one or more atoms that are NMR active, allowing the nanoparticles to be detected using NMR, both in vitro and in vivo. Examples of NMR active atoms include $Mn^{+2}$, $Gd^{+3}$, $Eu^{+2}$, $Cu^{+2}$, $V^{+2}$, $Co^{+2}$, $Ni^{+2}$, $Fe^{+2}$, $Fe^{+3}$ and lanthanides$^{+3}$, or the quantum dots described elsewhere in this application.

Nanoparticle cores comprising semiconductor atoms can be detected as nanometer scale semiconductor crystals are capable of acting as quantum dots, that is they can absorb light thereby exciting electrons in the materials to higher energy levels, subsequently releasing photons of light at frequencies characteristic of the material. An example of a semiconductor core material is cadmium selenide, cadmium sulphide, cadmium tellurium. Also included are the zinc compounds such as zinc sulphide.

In some embodiments, the core of the nanoparticles may be magnetic and comprise magnetic metal atoms, optionally in combination with passive metal atoms. By way of example, the passive metal may be gold, platinum, silver or copper, and the magnetic metal may be iron or gadolinium. In preferred embodiments, the passive metal is gold and the magnetic metal is iron. In this case, conveniently the ratio of passive metal atoms to magnetic metal atoms in the core is between about 5:0.1 and about 2:5. More preferably, the ratio is between about 5:0.1 and about 5:1. As used herein, the term "passive metals" refers to metals which do not show magnetic properties and are chemically stable to oxidation. The passive metals may be diamagnetic or superparamagnetic. Preferably, such nanoparticles are superparamagnetic.

Examples of nanoparticles which have cores comprising a paramagnetic metal, include those comprising $Mn^{+2}$, $Gd^{+3}$, $Eu^{+2}$, $Cu^{+2}$, $V^{+2}$, $Co^{+2}$, $Fe^{+2}$ $Fe^{+3}$ and lanthanides$^{+3}$.

Other magnetic nanoparticles may be formed from materials such as MnFe (spinel ferrite) or CoFe (cobalt ferrite) can be formed into nanoparticles (magnetic fluid, with or without the addition of a further core material as defined above. Examples of the self-assembly attachment chemistry for producing such nanoparticles is given in Biotechnol. Prog., 19:1095-100 (2003), J. Am. Chem. Soc. 125:9828-33 (2003), J. Colloid Interface Sci. 255:293-8 (2002).

In some embodiments, the nanoparticle of the present invention or one or more of its ligands comprises a detectable label. The label may be an element of the core of the nanoparticle or the ligand. The label may be detectable because of an intrinsic property of that element of the nanoparticle or by being linked, conjugated or associated with a further moiety that is detectable. Preferred examples of labels include a label which is a fluorescent group, a radionuclide, a magnetic label or a dye. Fluorescent groups include fluorescein, rhodamine or tetramethyl rhodamine, Texas-Red, Cy3, Cy5, etc., and may be detected by excitation of the fluorescent label and detection of the emitted light using Raman scattering spectroscopy (Y. C. Cao, R. Jin, C. A. Mirkin, Science 2002, 297: 1536-1539).

In some embodiments, the nanoparticles may comprise a radionuclide for use in detecting the nanoparticle using the radioactivity emitted by the radionuclide, e.g. by using PET, SPECT, or for therapy, i.e. for killing target cells. Examples of radionuclides commonly used in the art that could be readily adapted for use in the present invention include $^{99m}Tc$, which exists in a variety of oxidation states although the most stable is $TcO^{4-}$; $^{32}P$ or $^{33}P$; $^{57}Co$; $^{59}Fe$; $^{67}Cu$ which is often used as $Cu^{2+}$ salts; $^{67}Ga$ which is commonly used a $Ga^{3+}$ salt, e.g. gallium citrate; $^{68}Ge$; $^{82}Sr$; $^{99}Mo$; $^{103}Pd$; $^{111}In$ which is generally used as $In^{3+}$ salts; $^{125}I$ or $^{131}I$ which is generally used as sodium iodide; $^{137}Cs$; $^{153}Gd$; $^{153}Sm$; $^{158}Au$; $^{186}Re$; $^{201}Tl$ generally used as a $Tl^+$ salt such as thallium chloride; $^{39}Y^{3+}$; $^{71}Lu^{3+}$; and $^{24}Cr^{2+}$. The general use of radionuclides as labels and tracers is well known in the art and could readily be adapted by the skilled person for use in the aspects of the present invention. The radionuclides may be employed most easily by doping the cores of the nanoparticles or including them as labels present as part of ligands immobilised on the nanoparticles.

Additionally or alternatively, the nanoparticles of the present invention, or the results of their interactions with other species, can be detected using a number of techniques well known in the art using a label associated with the nanoparticle as indicated above or by employing a property of them. These methods of detecting nanoparticles can range from detecting the aggregation that results when the nanoparticles bind to another species, e.g. by simple visual inspection or by using light scattering (transmittance of a solution containing the nanoparticles), to using sophisticated techniques such as transmission electron microscopy (TEM) or atomic force microscopy (AFM) to visualise the nanoparticles. A further method of detecting metal particles is to employ plasmon resonance that is the excitation of electrons at the surface of a metal, usually caused by optical radiation. The phenomenon of surface plasmon resonance (SPR) exists at the interface of a metal (such as Ag or Au) and a dielectric material such as air or water. As changes in SPR occur as analytes bind to the ligand immobilised on the surface of a nanoparticle changing the refractive index of the interface. A further advantage of SPR is that it can be used to monitor real time interactions. As mentioned above, if the nanoparticles include or are doped with atoms which are NMR active, then this technique can be used to detect the particles, both in vitro or in vivo, using techniques well known in the art. Nanoparticles can also be detected using a system based on quantitative signal amplification using the nanoparticle-promoted reduction of silver (I). Fluorescence spectroscopy can be used if the nanoparticles include ligands as fluorescent probes. Also, isotopic labelling of the carbohydrate can be used to facilitate their detection.

The ligands may include an inert carbohydrate component (e.g. glucose) that permits to control at will the density of antigens and carrier in the final construct.

Infectious Agents

In some embodiments, the nanoparticles may incorporate one or more further ligands that are capable of producing a specific response to target infectious agent(s). By way of example, the ligand may comprise an antigen, e.g. a peptide antigen, from an infectious agent such as influenza, HIV, tuberculosis or malaria.

In the present invention, "infectious agent" includes the detrimental colonization of a host organism by a foreign species. Typically, the infecting organism or pathogen seeks to utilize the host's resources in order to multiply at the expense of the host, interfering with the normal functioning of the host. Infectious agents include a range of microscopic organisms such as bacteria, viruses, parasites, and fungi. Antigens from infectious agents are well known to those skilled in the art and may be used as ligands when designing and making the nanoparticles of the present invention.

By way of example, the present invention includes the use of nanoparticles having antigenic ligands for treating viral infectious diseases include AIDS, AIDS related complex, chickenpox (Varicella), common cold, cytomegalovirus infection, Colorado tick fever, Dengue fever, Ebola haemorrhagic fever, epidemic parotitis, flu, hand, foot and mouth disease, hepatitis, herpes simplex, herpes zoster, human papillomaviruses, influenza, lassa fever, measles, Marburg haemorrhagic fever, infectious mononucleosis, mumps, poliomyelitis, progressive multifocal leukencephalopathy, rabies, rubella, severe acute respiratory syndrome (SARS), smallpox (Variola), viral encephalitis, viral gastroenteritis, viral meningitis, viral pneumonia, West Nile disease and yellow fever. In a preferred embodiment, the present invention is directed to the treatment of influenza, and in particular avian influenza exemplified by strains such as the H5N1 virus.

By way of example, the present invention includes the use of nanoparticles having antigenic ligands for treating and prophylaxis bacterial infectious diseases include anthrax, bacterial meningitis, brucellosis, bubonic plague, Campylobacteriosis, cholera, diphtheria, epidemic typhus, gonorrhea, impetigo, Hansen's disease, *legionella*, leprosy, leptospirosis, listeriosis, Lyme's disease, melioidosis, MRSA infection, nocardiosis, pertussis, pneumococcal pneumonia, psittacosis, Q fever, Rocky Mountain spotted fever (RMSF), salmonellosis, scarlet fever, shigellosis, syphilis, tetanus, trachoma, tuberculosis, tularemia, typhoid fever, typhus and whooping cough.

By way of example, the present invention includes the use of nanoparticles having antigenic ligands for treating and prophylaxis of parasitic infectious diseases include African trypanosomiasis, amebiasis, amoebic infection, *ascariasis*, babesiosis, Chagas disease, clonorchiasis, cryptosporidiosis, cysticercosis, diphyllobothriasis, dracunculiasis, echinococcosis, enterobiasis, fascioliasis, fasciolopsiasis, filariasis, giardiasis, gnathostomiasis, hymenolepiasis, isosporiasis, kala-azar, leishmaniasis, malaria, metagonimiasis, myiasis, onchocerciasis, pediculosis, scabies, schistosomiasis, taeniasis, toxocariasis, toxoplasmosis, trichinellosis, trichinosis, trichuriasis and trypanosomiasis.

By way of example, the present invention includes the use of nanoparticles having antigenic ligands for treating fungal infectious diseases include *Aspergillosis, Blastomycosis, Candidiasis, Coccidioidomycosis, Cryptococcosis, Histoplasmosis* and *Tinea pedis*.

By way of example, the present invention includes the use of nanoparticles having antigenic ligands for treating prion infectious diseases include bovine spongiform encephalopathy, Creutzfeldt-Jakob disease and Kuru.

Influenza

The nanoparticles vaccines disclosed herein may be particularly useful for the prophylaxis and/or treatment of influenza, e.g. avian influenza such as the H5N1 strain. Multiple options present themselves for the use of the nanoparticles disclosed herein, but they can be classified into two basic areas, treatment and prevention.

Nanoparticle vaccines could be designed as disclosed herein. Nanoparticles with short peptides from hopefully conserved external protein regions such as H, N and possibly the M2 protein could be tried. While single peptide sequences could be employed, the use of multiple ones from the 2-3 main surface proteins are preferred to improve the chances of successful vaccination. These peptide sequences may require annual review in much the same way as current flu vaccines due to antigenic drift, but their wholly synthetic nature could make their production much easier and quicker than current in vivo techniques.

Influenza Virus

There are three serotypes of influenza virus: A, B, and C. Influenza A viruses are further categorized into subtypes based on the surface antigens, neuraminidase (N) and haemagglutinin (H). Additionally, strains are classified on geographical location of first isolation, serial number, and year of isolation. Influenza A and B cause most clinical disease. Influenza A occurs more frequently and is more virulent. It is responsible for most major epidemics and pandemics. Influenza B often co-circulates with influenza A during the yearly outbreaks. Generally, influenza B causes less severe clinical illness, although it can still be responsible for outbreaks. Influenza C usually causes a mild or asymptomatic infection similar to the common cold.

The influenza virus is made up of a lipid membrane that surrounds a protein shell and a core of separate RNA molecules. Three proteins are embedded in the lipid membrane of influenza types A and B; two glycoproteins that act as the major antigenic determinant of influenza type A and B—N antigen and H antigen—and a small membrane channel protein. Neuraminidase facilitates the release of new virions from infected host cells, while haemagglutinin facilitates the entry of virus into respiratory epithelial cells. The membrane channel for influenza A is known as the M2 protein, and for influenza B is known as the NB protein. Differences in the structure of the membrane channel are associated with different susceptibility to the antiviral agent, amantadine.

The influenza virus attaches to epithelial cells of the upper and lower respiratory tract, invades the host cell and then uses it to reproduce. Virions are released when the host cell is lysed. The subsequent breaches in the respiratory epithelium result in an increased susceptibility to secondary viral and bacterial infection.

Influenza Virus Vaccines

There are two types of vaccines that protect against the flu. The well known "flu shot" is an inactivated vaccine (containing killed virus) that is given with a needle, usually in the arm. A different kind of vaccine, called the nasal-spray flu vaccine (sometimes referred to as LAIV for Live Attenuated Influenza Vaccine), was approved in 2003. The nasal-spray flu vaccine contains attenuated (weakened) live viruses, and is administered by nasal sprayer. It is approved for use only among healthy people between the ages of 5 and 49 years. The flu shot is approved for use among all people over 6 months of age, including healthy people and those with chronic medical conditions.

Each of the two vaccines contains three influenza viruses, representing one of the three groups of viruses circulating among people in a given year. Each of the three vaccine strains in both vaccines, for example; one A (H3N2) virus, one A (H1N1) virus, and one B virus that are representative of the influenza vaccine strains recommended for that year. Viruses for both vaccines are grown in hens eggs. All current flu vaccines with the exception of the ones listed below and experimental ones are attenuated whole viruses. There are 2 main reasons why whole viruses are used; there are many mutations/shifts that occur to the flu N/H coat proteins during and epidemic, a single mutation could render the current year vaccine worthless, many mutations though would be required to render whole virus vaccines useless and secondly peptides are not strongly immunogenic.

Anti-Viral Drugs Used Against Influenza

There are very few treatments that work on viruses, those that work on influenza need to be given within 48 hours of the onset of the attack, often before it is possible to be absolutely sure of the diagnosis, they only shorten and reduce the severity of the condition. Prevention with influenza vaccine is the best option.

There are now three influenza treatments licensed for use in the UK: amantidine (Synmetrel, Lysovir) and oseltamivir (Tamiflu), both of which are taken orally, and zanamivir (Relenza), which is provided as a powder that is inhaled. Oseltamivir and zanamivir are neuraminidase inhibitors and are licensed for treatment of both the main types of influenza in humans (type A and type B). Amantidine and a derivative rimantadine have the benefit of being less expensive, but they only work on type A influenza.

Once new viral particles are formed, they leave the epithelial cell and disperse to other cells, where the infective process is repeated. The surface enzyme that enables new viruses to leave cells, allowing them to spread the infection to neighboring cells within the respiratory tract, is the viral neuraminidase. This enzyme action is blocked by zanamivir and oseltamivir. Without the neuraminidase, the virus is unable to spread to other cells and the infection subsides.

Amantidine is classed as a M2 ion channel blocker, its is not prescibed often due to the rapid development of drug resistant flu variants, and the fact that it has no activity against B type flu.

Current Clinical Guidelines

None of these drugs (amantidine, oseltamivir, and zanamivir) is recommended for treatment or prevention of influenza in children or adults unless they are in the at risk groups. Both oseltamivir and zanamivir are recommended for the treatment of at risk adults who can start treatment within 48 hours of the onset of symptoms. Oseltamivir is also recommended for the treatment of at risk children who can start treatment within 48 hours of the onset of symptoms. Amantidine is not recommended for the treatment or prevention of influenza.

Administration and Treatment

The nanoparticle compositions of the invention may be administered to patients by any number of different routes, including enteral or parenteral routes. Parenteral administration includes administration by the following routes: intravenous, cutaneous or subcutaneous, nasal, intramuscular, intraocular, transepithelial, intraperitoneal and topical (including dermal, ocular, rectal, nasal, inhalation and aerosol), and rectal systemic routes.

Administration be performed e.g. by injection, or ballistically using a delivery gun to accelerate their transdermal passage through the outer layer of the epidermis. The nanoparticles can then be taken up, e.g. by dendritic cells, which mature as they migrate through the lymphatic system, resulting in modulation of the immune response and vaccination against the antigen. The nanoparticles may also be delivered in aerosols. This is made possible by the small size of the nanoparticles.

The exceptionally small size of the nanoparticles of the present invention is a great advantage for delivery to cells and tissues, as they can be taken up by cells even when linked to targeting or therapeutic molecules.

The nanoparticles of the invention may be formulated as pharmaceutical compositions that may be in the forms of solid or liquid compositions. Such compositions will generally comprise a carrier of some sort, for example a solid carrier such as gelatine or an adjuvant or an inert diluent, or a liquid carrier such as water, petroleum, animal or vegetable oils, mineral oil or synthetic oil. Physiological saline solution, or glycols such as ethylene glycol, propylene glycol or polyethylene glycol may be included. Such compositions and preparations generally contain at least 0.1 wt % of the compound.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, solutions of the compounds or a derivative thereof, e.g. in physiological saline, a dispersion prepared with glycerol, liquid polyethylene glycol or oils.

In addition to one or more of the compounds, optionally in combination with other active ingredient, the compositions can comprise one or more of a pharmaceutically acceptable excipient, carrier, buffer, stabiliser, isotonicising agent, preservative or anti-oxidant or other materials well known to those skilled in the art. Such materials should be non-toxic and should not interfere with the efficacy of the active ingredient. The precise nature of the carrier or other material may depend on the route of administration, e.g. orally or parenterally.

Liquid pharmaceutical compositions are typically formulated to have a pH between about 3.0 and 9.0, more preferably between about 4.5 and 8.5 and still more preferably between about 5.0 and 8.0. The pH of a composition can be maintained by the use of a buffer such as acetate, citrate, phosphate, succinate, Tris or histidine, typically employed in the range from about 1 mM to 50 mM. The pH of compositions can otherwise be adjusted by using physiologically acceptable acids or bases.

Preservatives are generally included in pharmaceutical compositions to retard microbial growth, extending the shelf life of the compositions and allowing multiple use packaging. Examples of preservatives include phenol, meta-cresol, benzyl alcohol, para-hydroxybenzoic acid and its esters, methyl paraben, propyl paraben, benzalconium chloride and benzethonium chloride. Preservatives are typically employed in the range of about 0.1 to 1.0 t (w/v).

Preferably, the pharmaceutically compositions are given to an individual in a prophylactically effective amount or a therapeutically effective amount (as the case may be, although prophylaxis may be considered therapy), this being sufficient to show benefit to the individual. Typically, this will be to cause a therapeutically useful activity providing benefit to the individual. The actual amount of the compounds administered, and rate and time-course of administration, will depend on the nature and severity of the condition being treated. Prescription of treatment, e.g., decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Handbook of Pharmaceutical Additives, 2nd Edition (eds. M. Ash and I. Ash), 2001 (Synapse Information Resources, Inc., Endicott, New York, USA); Remington's Pharmaceutical Sciences, 20th Edition, 2000, pub. Lippincott, Williams & Wilkins; and Handbook of Pharmaceutical Excipients, 2nd edition, 1994. By way of example, and the compositions are preferably administered to patients in dosages of between about 0.01 and 100 µg of active compound per kg of body weight, and more preferably between about 0.5 and 10 µg/kg of body weight.

Compositions of the nanoparticles of the present invention may be used as vaccines. In the present invention, the term "vaccination" includes an active immunization, that is an induction of a specific immune response due to administration, e.g. via the subcutaneous, intradermal, intramuscular, oral or nasal routes, of small amounts of an antigen which is recognized by the vaccinated individual as foreign and is therefore immunogenic in a suitable formulation. The antigen is thus used as a "trigger" for the immune system in order to build up a specific immune response against the antigen. The vaccination may be therapeutic or prophylactic.

EXPERIMENTAL

Nanoparticle Vaccines $HAuCl_4$ and $NaBH_4$ for making nanoparticles may be purchased from Aldrich Chemical Company. For all experiments and solutions, Nanopure water (18.1 mΩ) may be used. The nanaoparticles disclosed herein may be prepared using the methodology disclosed in WO 02/32404 and WO 2004/108165. The mean diameters of these constructs may be determined using transmission electron microscopy (TEM).

The preparation and characterization of nanoparticles loaded with the ligands that include (a) a first ligand comprising a carbohydrate antigen capable of stimulating an innate immune response (b) a second ligand comprising a T cell helper peptide and (c) a third ligand comprising a danger signal as follows. The nanoparticles may also include glucose ligands and optionally also one or more further ligands that are capable of producing a specific response to a target infectious agent. The selection of antigens suitable for raising immune responses against avian flu, and in particular strain H5N1 is described below.

The carbohydrate ligands, either glucose ligands or the first ligand comprising a carbohydrate antigen capable of stimulating an innate immune response (GlnAc) may be incorporated in the nanoparticles using a $C_{2-5}$ aliphatic spacer to attach the ligands to the gold surface.

Other ligands such as the T-helper peptide ligand or the danger signal (the endotoxin labelled "Adj" in FIG. 1) may be prepared by linking the relevant species using a Cu aliphatic spacer, e.g. the promiscuous T-cell peptide epitope (FKLQTMVKLFNRIKNNVA; SEQ ID NO: 1) from tetanus toxoid through the amino terminal group to a Cu aliphatic spacer.

$^1$H NMR spectra can be taken of solutions of the nanoparticles at 500 MHz to identify signals unequivocally belonging to the individual ligand components and to confirm that the intensity of these signals corresponded to those expected according to the ratio of the different ligands in the original solution. After diluting with methanol, the glyconanoparticles may be repeatedly purified by centrifugal filtering.

Figure 2A:
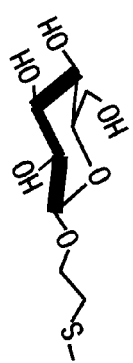
FIG. 2 shows the structures of the individual ligands shown schematically in FIG. 1.
2a Glc=glucose
2b GlcNAc=n-acetylglucosamine
2c TT=tetanus toxin (promiscuous T-helper peptide)
2d N1=avian influenza virus peptide antigen
2e H5=avian influenza virus peptide antigen
2f M=malaria antigen
2g Adj=lipid danger signal
Figure 2B:
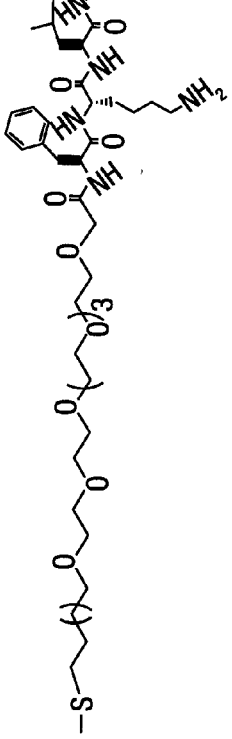
Figure 2C:
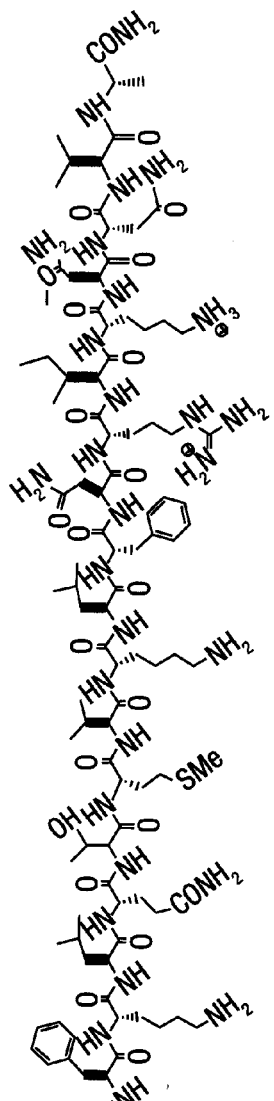
Figure 2D:
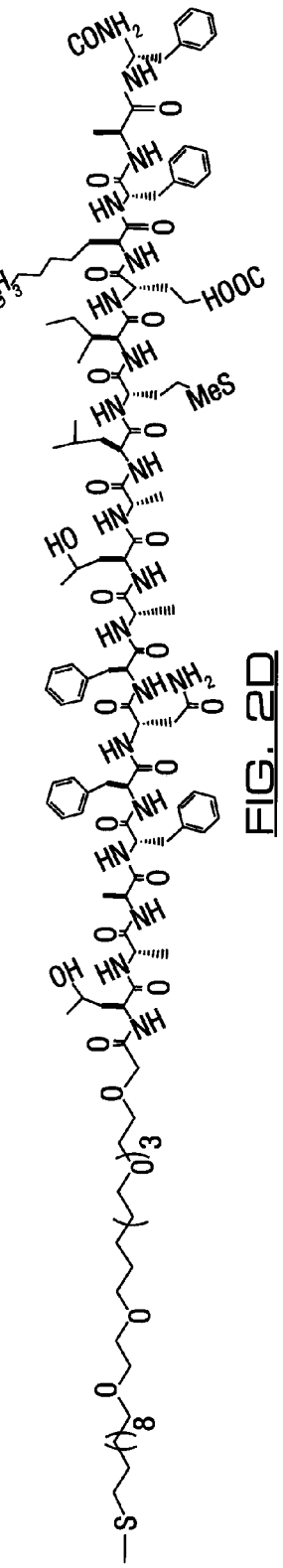
Figure 2E:
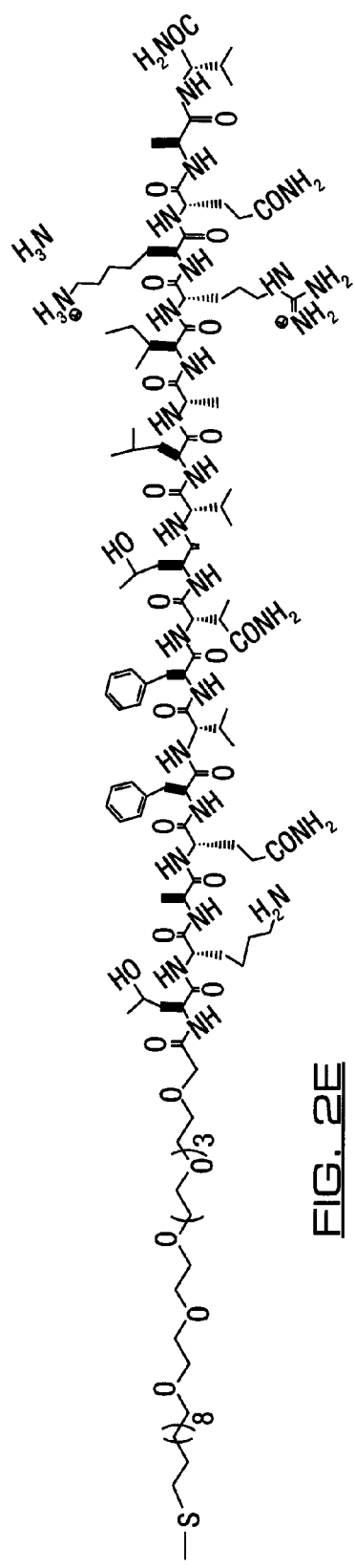
Figure 2F:
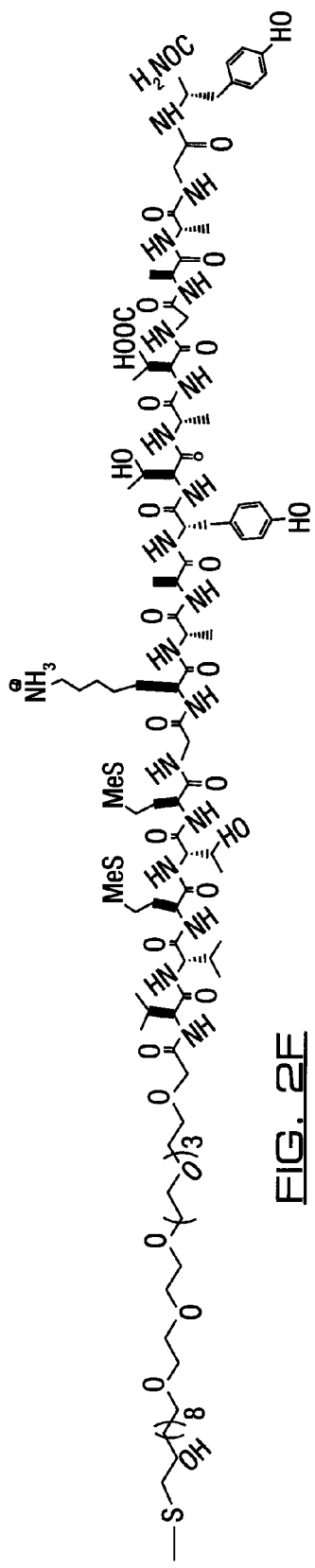
Figure 2G:
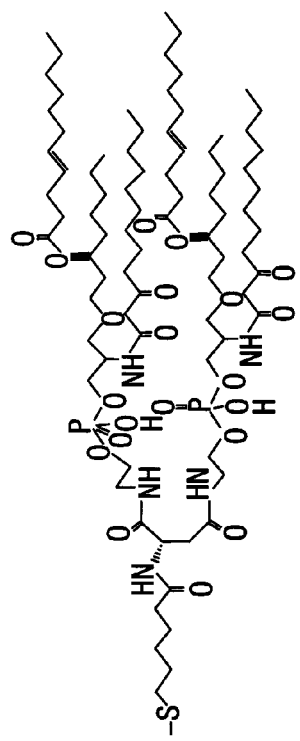

A nanoparticle for the prophylactic or therapeutic vaccination against the H5N1 strain of avian influenza was designed. The nanoparticle has a metallic core, e.g. formed from gold atoms, and is produced by self assembly of thiolated ligands. The nanoparticle has a corona of glucose ligands (Glc, FIG. 1) to help make the parts of it other than the four ligands described below invisible to the immune system. The first ligand comprises N-acetyl glucosamine sugar moieties (GlnAc, FIG. 1) to make the nanoparticle resemble a bacterial fragment to stimulate the innate immune response from the carbohydrate-based recognition system normally resulting in lectinophagocytosis of the bacterial or yeast (see Rademacher et al, Chapter 11, Abnormalities in IgG Glycosylation and Immunological Disorders, Ed Isenberg & Rademacher, John Wiley, 1996, p 221-252). The second ligand is a T-helper peptide and is shown in FIG. 1 as "TT" and in this example is a promiscuous tetanus toxin peptide sequence. The third ligand is the danger signal and is shown in FIG. 1 as "Adj" and is a lipid ligand as shown in FIG. 2g. The fourth type of ligands comprise antigenic peptides the H5N1 avian influenza strain (H5 and N1 in FIG. 1). The nanoparticle vaccine may also be polyvalent by including different antigenic ligands, e.g. in FIG. 1 including malaria epitopes (M). The fourth ligands may comprise either or both B cell and T cells epitopes deduced from the infectious agent against which the vaccine is directed.

Identification of Antigenic Avian Flu Epitopes

The complete sequences of the proteins of the H5N1 influenza strain are provided in Puthavathana et al, "Molecular characterization of the complete genome of human influenza H5N1 virus isolates from Thailand", J. Gen. Virol. 86 (Part 2): 423-433, (2005), (PUBMED 15659762). This sequence may be used as described herein or using other techniques well known in the art to find peptide sequences suitable for use as ligands in accordance with the nanoparticle vaccines of the present invention.

The sequences of A/Thailand/2 (SP-33)/2004 (H5N1), that was isolated from a 7 year old boy, was analysed for antigenic peptide sequences for use as ligands in the nanoparticle vaccines of the present invention. HA receptor binding site amino acids for this strain and others is strongly conserved and are 91 Y, 130-34 GVSSA (SEQ ID NO: 2), 149 W, 151 I, 179 H, 186 E, 190-1 LY and 220-25 NGQSGR (SEQ ID NO: 3) shown underlined in the sequence of FIG. 3 and in the peptide sequences below. This sequence includes 16 αα leader sequence (bold), numbers above from actual protein with leader removed, therefore add 16 to relate to sequence below—SWISSPROT Q6Q791.

When trying to target regions for antibody based vaccines, the HA receptor binding site amino acids are useful targets, as antibodies may not only clear viral load, but also prevent attachment to hosts in addition to being highly conserved sequences. We used Abie Pro 3.0 to select antigenic peptides from HA, with a minimum length of 10 amino acids, high specificity, avoiding CHM amino acids, N-linked amino acids and kinase sites. This found:

| | |
|---|---|
| YIVEKANPVNDL | (SEQ ID NO: 4) |
| YPGDFNDYEEL | (SEQ ID NO: 5) |
| EKIQIIPKSS | (SEQ ID NO: 6) |
| PYQGKSSFFRNV | (SEQ ID NO: 7) |
| PNDAAEQTKLYQ | (SEQ ID NO: 8) |
| STLNQRLVPR | (SEQ ID NO: 9) |
| LKPNDAINFESNGNFIA | (SEQ ID NO: 10) |
| ESNGNFIAPEYA | (SEQ ID NO: 11) |
| APEYAYKIVKKGDSTI | (SEQ ID NO: 12) |
| SNEQGSGYAAA | (SEQ ID NO: 13) |
| AVGREFNNLER | (SEQ ID NO: 14) |
| DSNVKNLYDKVRLQ | (SEQ ID NO: 15) |
| EARLKREEISGVKLESI | (SEQ ID NO: 16) |

Possible 10 oligomer including aa involved in HA binding site are reported below with the hydrophilicity of the peptide given in parentheses.

In both of these peptides, some of the amino acids are partially hidden in the HA structure:

```
                                           (SEQ ID NO: 17)
YPGDFNDYEE (0.5) 107-116 located on the
side of the head.

(SEQ ID NO: 18)
DAAEQTKLYQ (0.4) 199-208 near the top
of the head.
```

In addition, the following two 10 oligomers were identified as near linear stretches exposed on the head of HA using AstexViewer in SWISSPROT 3D:

```
RIATESKVNG (0.5) 228-237        (SEQ ID NO: 19)

NDAINFESNG (0.2) 252-261        (SEQ ID NO: 20)
```

Antigenic peptides can also be determined using the method of Kolaskar and Tongaonkar (1990), FEES lett. 1990 Dec. 10; 276 (1-2):172-4. Predictions are based on a table that reflects the occurrence of amino acid residues in experimentally known segmental epitopes. Segments are only reported if the have a minimum size of 8 residues. The reported accuracy of method is about 75%.

This found 22 candidate peptides (see Table 1) of which many of the sequences were primarily internal and therefore are not suitable targets. Others belong to HA2 and are likely to be difficult/poor targets being on the tail, transmembrane or cytosolic regions. The method did suggest a section of peptide 2 DLDGVKPLIL (SEQ ID NO: 21), which is high on the HA tail which is a possible target candidate, peptide 6 EKIQIIPKSS (SEQ ID NO: 22) has been extended to a 10 oligomer by the addition of SS it appears on the lower/mid side of the HA head, peptide 12 STLNQRLVPR (SEQ ID NO: 23) looks the best its located on the top/mid of the head and is essentially fully external, and ST was been added to make a 10 oligomer. Thus, by this method, three peptides were selected, and are presented in order of preference, top first:

```
STLNQRLVPR 219-228 (0.1)        (SEQ ID NO: 23)

EKIQIIPKSS 128-137 (0.4)        (SEQ ID NO: 22)

DLDGVKPLIL 59-68 (0.0)          (SEQ ID NO: 21)
```

Note that LIL is a highly hydrophobic tail which makes the sequence less attractive as it may be difficult to synthesize by chemical techniques.

In summary, the selection of 10 oligomers by the three different criteria found that if just one peptide is to be made from each of the three groups it is suggested that those marked * are chosen, primarily due to their position and physicochemical properties. Possible cleavage/attachment amino acids have not been included.

A Short Blast search was used to check for similar sequences in human proteins, no complete matches were found, however, all peptides gave low score hits values (as shown below).

```
                                           (SEQ ID NO: 17)
YPGDFNDYEE (0.5) 107-116 (blast top score
26.9 max 5aa)
```

```
                                           (SEQ ID NO: 18)
DAAEQTKLYQ (0.4) 199-208* (23.1 several 5aa)

(SEQ ID NO: 19)
RIATRSKVNG (0.5) 228-237 (21.4 several 6aa)

(SEQ ID NO: 20)
NDAINFESNG (0.2) 252-261* (25.7 mainly 4aa)

(SEQ ID NO: 23)
STLNQRLVPR (0.1) 219-228* (24.4 some 6aa)

(SEQ ID NO: 22)
EKIQIIPKSS (0.4) 128-137 (24 some 6aa)

(SEQ ID NO: 21)
DLDGVKPLIL (0.0) 59-68 (22.7 some 6aa)
```

Finally, using the SIM alignment tool for the EA sequences for an H5N1 from Scotland in 1959 (P09345) and the 2004 sequence (Q6Q791), a screen for conserved or heavily mutated peptide sequences was carried out to try and determine whether or not the peptides selected by the above criteria were prone to mutation. Numbers and positions of mutations (in bold) are shown below;

```
YPGDFNDYEE      (SEQ ID NO: 17)     0
DAAEQTKLYQ      (SEQ ID NO: 18)     0
RIATRSKVNG      (SEQ ID NO: 19)     2
NDAINFESNG      (SEQ ID NO: 20)     0
STLNQRLVPR      (SEQ ID NO: 23)     3
EKIQIIPKSS      (SEQ ID NO: 22)     2
DLDGVKPLIL      (SEQ ID NO: 21)     2
```

Given the previous criteria set out above, this data highlights the suitability of the peptides DAAEQTKLYQ (SEQ ID NO: 18) and NDAINFESNG (SEQ ID NO: 20), but suggests that perhaps YPGDFNDYEE be included instead of STLNQRLVPR (SEQ ID NO: 23).

Regarding neuraminidase, the following peptides are possible although as no 3D structure has been analysed it is less certain that the regions are fully external.

```
247-258     EKGKVVKSVEL     (SEQ ID NO: 24)

308-320     GVFGDNPRPNDG    (SEQ ID NO: 25)

412-422     VELIRGRPKE      (SEQ ID NO: 26)
```

Identification of High Affinity Human MHC I Binding Peptides from H1N1 SP33 Proteins A study was also carried out to identify MHC I binding peptides in H5N1 SP33 proteins. RANKPEP search engine was used throughout, located at: http://www.mifoundation.org/Tools/rankpep.html. T-cell epitope immunogenicity is contingent on several factors: (1) appropriate and effective processing of a peptide from its protein source, (2) stable peptide binding to the MHC molecule, and (3) the ability of the TCR to recognize MHC-bound peptide. Computational modelling of these three processes is required for accurate prediction of T-cell epitopes. Usually only peptide MHC-binding, and processing of peptides for MHC class I restricted epitopes, have been considered in epitope prediction algorithms. RANKPEP also has a predictive model for immunodominant recognition of peptides by the TCR but in this study this option was disabled.

The C-terminus of MHC I restricted peptides is generated by the proteosome, RANKPEP can determine whether the C-terminus of the predicted MHCI-peptide binders is the result of proteosomal cleavage, only such peptides are included below. Sequences given below are for the top three binding peptides (if applicable) above the binding threshold, all of them are predicted to be produced by C terminal proteosomal cleavage.

It is hoped that by concentrating on the 5 HLA supertypes; A2, A3, A24, B7 and B15 that over 95% of the human population will be covered considering all possible phenotypical variations. The individual supertype alleles are shown below:

A2: A*0201, A*0202, A*0203, A*0205, A*0206, A*0207, A6802

A3: A*0301, A*1101, A*3101, A*3301, A*6801, A*6601

A24: A*2402, B*3801

B7: B*0702, B*3501, B*5101, B*5102, B*5301, B*5401

B15: A*0101, B*1501B62, B1502

When the HLA supertype failed to provide any peptides for a specific protein, the individual alleles were also tested, i.e. see HLA A24 below. It should be recognized though that if for example the MP1 HLA-A2402 peptide were included in a theoretical mixed vaccine, population coverage would be reduced by a few % compared to a fully HLA A24 supertype positive peptide.

Peptide Selection

Peptide selection was carried out on the basis of HLA binding, the hydrophobicity of the peptides and a BLAST search to determine whether any of the sequence occur in man. These studies may be used to decide whether to use peptides from a single protein in an infectious agent or a mixture of peptides, e.g. from different proteins.

However, the techniques reported herein for the identification of the peptides may be adapted by the skilled person as needed in a given situation. In the study carried out below, the H5N1 proteins used were MP1 as it is a major virion component and HA, NA and BP1.

The highest scoring peptides for HLA binding were run through another program 'Epigen' (http://www.jenner.ac.uk/EpiJen/), this program has additional algorithms that help to further refine the selected peptides, however, the allele specificity is more restricted than the RANKPEP program which is why it has been used as a secondary screening tool.

Blast searches were then performed on these peptides to determine if any of these viral sequences occur naturally in man. Blast searches used the NCBI site, and the 'nr' database, PAM 30 matrix (short peptides) and restricting the search to *Homo sapiens*. Ideally, candidate peptides should have low scores and high E values, the highest scoring match for each of the above peptides is shown in order below. 100* homologies for example when ELDAPNYHY the last peptide below is subjected to Blast 'viral' proteins, Flu neuraminidase is identified with a score of 34.6 and an E value of 0.03.

| Sequence | Human protein | Score | E value | SEQ ID NO: |
|---|---|---|---|---|
| QMVQAMRTI | UDP-galactose-4-epimerase | 24.8 | 16 | 27 |
| LLFAIVSLV | CD200 antigen | 22.7 | 68 | 28 |
| GMVSLMLQI | PCSK7 protein | 26.1 | 6.5 | 29 |
| LLIDGTASL | SNARE protein kinase SNAK | 21.4 | 164 | 30 |
| SIIPSGPLK | KIAA0596 splice variant 1 | 21.8 | 122 | 31 |
| AAAKESTQK | testis-specific poly(A)-binding P | 21.4 | 164 | 32 |
| SIHTGNQHK | Similar to hemicentin 1 | 22.3 | 91 | 33 |
| SMVEAMVSR | zinc finger, BED domain containing | 22.7 | 68 | 34 |
| LYKKLKREI | hypothetical protein LOC256369 | 23.5 | 38 | 35 |
| IYSTVASSL | intestinal mucin | 24.4 | 21 | 36 |
| AYGVKGFSF | Glypican 6, precursor | 23.5 | 38 | 37 |
| SYLIRALTL | neurotransmitter transporter RB21A | 25.2 | 12 | 38 |
| DPNNMDRAV | SNX13 protein | 21.4 | 164 | 39 |
| APEYAYKIV | G protein-coupled receptor 123 | 21.8 | 122 | 40 |
| NPNKKIITI | M-phase phosphoprotein 1 | 22.3 | 91 | 41 |
| GPATAQMAL | Rho GTPase-activating protein | 22.7 | 68 | 42 |
| ELDAPNYHY | Low-density lipoprotein receptor | 23.1 | 51 | 43 |

Interpretation of these Blast results is both difficult and important because most of these peptides above contain between 4, 5 and even 6 amino acids that are identical to those found in various human proteins. Accordingly the effect of these regions of similarity will have to be investigated further in subjects submitted to vaccination with these peptides. If selection were made on the basis of the E values, it may be best to ignore GMVSLMLQI and SYLIRALTL. This leaves 15 target peptides. Similar analysis could be performed on the other 6 H5N1 proteins if more peptides are required.

TABLE 1

| n | Start Position | Sequence | End Position | SEQ ID NO: |
|---|---|---|---|---|
| 1 | 22 | KNVTVTHAQD | 31 | 44 |
| 2 | 38 | NGKLCDLDGVKPLILRDCSVAG | 59 | 45 |
| 3 | 69 | EFINVPEWSYIVEK | 82 | 46 |
| 4 | 85 | PVNDLCYP | 92 | 47 |
| 5 | 99 | EELKHLLSR | 107 | 48 |
| 6 | 112 | EKIQIIPK | 119 | 49 |
| 7 | 123 | SSHEVSLGVSSACPYQGK | 140 | 50 |
| 8 | 143 | FFRNVVWL | 150 | 51 |
| 9 | 170 | EDLLVLWG | 177 | 52 |
| 10 | 186 | EQTKLYQ | 192 | 53 |
| 11 | 196 | TYISVGT | 202 | 54 |
| 12 | 205 | LNQRLVPR | 212 | 55 |
| 13 | 248 | IAPEYAYKIVK | 258 | 56 |
| 14 | 274 | CNTKCQT | 280 | 57 |
| 15 | 290 | PFHNIHPLTIGECPKYVKSNRLVLA | 314 | 58 |
| 16 | 332 | LFGAIAG | 338 | 59 |
| 17 | 417 | GFLDVWT | 423 | 60 |
| 18 | 425 | NAELLVL | 431 | 61 |
| 19 | 445 | VKNLYDKVRL | 454 | 62 |
| 20 | 467 | CFEFYHKCD | 475 | 63 |
| 21 | 503 | ISGVKLESIGIYQILSIYSTVASSLALAIMVAGLSLWM | 540 | 64 |
| 22 | 542 | SNGSLQC | 548 | 65 |

REFERENCES

The references mentioned herein are all expressly incorporated by reference in their entirety.

[1] J. M. de la Fuente, A. G. Barrientos, T. C. Rojas, J. Canada, A. Fernández, S. Penadés, *Angew. Chem. Int. Ed.*, 2001, 40, 2257.

[2] A. G. Barrientos, J. M. de la Fuente, T. C. Rojas, A. Fernández, S. Penadés, *Chem. Eur. J.*, 2003, 9, 1909.

[3] M. J. Hostetler, J. E. Wingate, C. Z. Zhong, J. E. Harris, R. W. Vachet, M. R. Clark, J. D. Londono, S. J. Green, J. J. Stokes, G. D. Wignall, G. L. Clish, M. D. Porter, N. D. Evans, R. W. Murray, *Langmuir*, 1998, 14, 17.

[4] This methanolic layer was concentrated under reduced pressure. The $^1$H-NMR spectrum of the residue showed the same initial ratio, approximately, between Glc, STn, Le$^y$ and BC11 signals.

The invention claimed is:

1. A method of preparing nanoparticles which comprise a core including metal and/or semiconductor atoms, wherein the core is covalently linked to a plurality of ligands, the ligands including:
   (a) a first ligand comprising a carbohydrate residue capable of stimulating an innate immune response;
   (b) a second ligand comprising a T cell helper peptide;
   (c) a third ligand comprising a danger signal selected from the group consisting of endotoxins, heat-shock proteins, nucleotides, reactive oxygen intermediates, extracellular-matrix breakdown products, neuromediators, cytokines and lipid moieties, wherein said danger signal is a toll-like receptor agonist; and
   (d) one or more ligands capable of producing a specific response to a target infectious agent, said nanoparticles further comprising a corona of ligands comprising carbohydrate groups capable of shielding the nanoparticles from recognition by an immune system, so that the immune response produced by the nanoparticles in vivo is specific to the target infectious agent, by conjugating one or more of the ligands to the nanoparticle core, the method comprising: (i) derivatizing the one or more ligands with a linker; and (ii) reacting the linker derivatized ligands with reactants for producing the core of the nanoparticle so that during self-assembly of the nanoparticles, the nanoparticle cores attach to the ligands via the linker.

2. The method of claim 1, wherein the linker group comprises a thiol group, an alkyl group, a glycol group or a peptide group.

3. The method of claim 1, wherein the linker group comprises C2-C15 alkyl and/or C2-C15 glycol.

4. The method of claim 1, wherein the linker group is C2-C15 alkyl or hexaethylene glycol-C11 alkyl.

5. The method of claim 1, wherein the reaction mixture comprises the one or more linker derivatized ligands, a salt of the metal and/or semiconductor atoms and a reducing agent to produce the nanoparticles.

* * * * *